US006610040B1

(12) United States Patent
Fowles et al.

(10) Patent No.: US 6,610,040 B1
(45) Date of Patent: *Aug. 26, 2003

(54) SLIDING RECONSTITUTION DEVICE WITH SEAL

(75) Inventors: Thomas A. Fowles, McHenry, IL (US); Thomas J. Progar, Grays Lake, IL (US); Robert J. Weinberg, McHenry, IL (US); Craig A. Fuller, Antioch, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,033

(22) Filed: May 8, 2000

Related U.S. Application Data

(63) Continuation of application No. 08/986,580, filed on Dec. 4, 1997, now Pat. No. 6,071,270.

(51) Int. Cl.[7] .................................... A61M 5/32

(52) U.S. Cl. .......................... 604/413; 604/414; 604/88

(58) Field of Search ......................... 604/403, 411–414, 604/905

(56) References Cited

U.S. PATENT DOCUMENTS

| | | |
|---|---|---|
| 3,330,281 A | 7/1967 | Visser |
| 3,330,282 A | 7/1967 | Visser et al. |
| 3,336,924 A | 8/1967 | Sarnoff et al. |
| 3,785,481 A | 1/1974 | Allet-Coche |
| 3,796,303 A | 3/1974 | Allet-Coche |
| 3,809,225 A | 5/1974 | Allet-Coche |
| 3,917,063 A | 11/1975 | Chibret et al. |
| 4,014,330 A | 3/1977 | Genese |
| 4,031,895 A | 6/1977 | Porter |
| 4,059,112 A | 11/1977 | Tischlinger |
| 4,116,196 A | 9/1978 | Kaplan et al. |
| 4,170,994 A | 10/1979 | Komatsu |
| 4,210,142 A | 7/1980 | Wörder |

(List continued on next page.)

FOREIGN PATENT DOCUMENTS

| | | |
|---|---|---|
| DE | 1913926 | 9/1970 |
| DE | 1766151 | 3/1971 |
| EP | 0 022 977 A1 | 1/1981 |
| EP | 0 091 310 A2 | 12/1983 |
| EP | 0 285 424 A1 | 5/1988 |
| EP | 0 335 378 A2 | 4/1989 |
| EP | 0 363 770 A1 | 4/1990 |
| EP | 0 395 758 A1 | 7/1990 |
| EP | 0 499 764 A1 | 8/1991 |
| EP | 0 692 235 A1 | 7/1994 |

(List continued on next page.)

*Primary Examiner*—Angela D. Sykes
*Assistant Examiner*—Leslie R. Deak
(74) *Attorney, Agent, or Firm*—Wallenstein & Wagner

(57) ABSTRACT

The present invention provides a connector device for establishing fluid communication between a first container and a second container. The device has a first sleeve member having a first and a second end, the first sleeve member having at the first end a first attaching member adapted to attach to the first container. The device further has a second sleeve member having a first end and a second end, the second sleeve member being associated with the first sleeve member and movable with respect thereto from an inactivated position to an activated position, the second sleeve member having at the second end a second attaching member adapted to attach the second sleeve member to the second container. First and second piercing members project from one of the first and second sleeve members for providing a fluid flow path from the first container to the second container, and the first and second piercing members are independently hermetically sealed.

43 Claims, 6 Drawing Sheets

U.S. PATENT DOCUMENTS 4,210,173 A 7/1980 Choksi et al.
4,226,330 A 10/1980 Butler
4,243,080 A 1/1981 Choksi et al.
4,247,651 A 1/1981 Ohno et al.
4,270,533 A 6/1981 Andreas
4,303,071 A 12/1981 Smith
4,328,802 A 5/1982 Curley et al.
4,392,850 A 7/1983 Elias et al.
4,396,383 A 8/1983 Hart
4,410,321 A 10/1983 Pearson et al.
4,411,358 A 10/1983 Bennwik et al.
4,411,662 A 10/1983 Pearson
4,424,056 A 1/1984 Urquhart et al.
4,424,057 A 1/1984 House
4,432,754 A 2/1984 Urquhart et al.
4,432,755 A 2/1984 Pearson
4,432,756 A 2/1984 Urquhart et al.
4,439,182 A 3/1984 Huang
4,439,183 A 3/1984 Huang
4,458,733 A 7/1984 Lyons
4,458,811 A 7/1984 Wilkinson
4,465,471 A 8/1984 Harris et al.
4,465,488 A 8/1984 Richmond et al.
4,467,588 A 8/1984 Carveth
4,469,872 A 9/1984 Anderson et al.
4,474,574 A 10/1984 Wolfe et al.
4,479,793 A 10/1984 Urquhart et al.
4,479,794 A 10/1984 Urquhart et al.
4,484,909 A 11/1984 Urquhart et al.
4,484,920 A 11/1984 Kaufman et al.
4,493,703 A 1/1985 Butterfield
4,496,646 A 1/1985 Ito
4,505,709 A 3/1985 Froning et al.
4,507,113 A 3/1985 Dunlap
4,507,114 A 3/1985 Bohman et al.
4,511,351 A 4/1985 Theeuwes
4,511,352 A 4/1985 Theeuwes et al.
4,511,353 A 4/1985 Theeuwes
4,515,351 A 5/1985 Nakayama et al.
4,515,585 A 5/1985 Urquhart et al.
4,516,967 A 5/1985 Kopfer
4,516,977 A 5/1985 Herbert
4,518,386 A 5/1985 Tartaglia
4,519,499 A 5/1985 Stone et al.
4,521,211 A 6/1985 Theeuwes
4,525,162 A 6/1985 Urquhart et al.
4,533,348 A 8/1985 Wolfe et al.
4,534,757 A 8/1985 Geller
4,534,758 A 8/1985 Akers et al.
4,538,918 A 9/1985 Mittleman
4,539,793 A 9/1985 Malek
4,540,089 A 9/1985 Maloney
4,540,403 A 9/1985 Theeuwes
4,543,094 A 9/1985 Barnwell
4,543,101 A 9/1985 Crouch
4,548,598 A 10/1985 Theeuwes
4,548,599 A 10/1985 Urquhart et al.
4,548,606 A 10/1985 Larkin
4,550,825 A 11/1985 Sutryn et al.
4,552,277 A 11/1985 Richardson et al.
4,552,555 A 11/1985 Theeuwes
4,552,556 A 11/1985 Urquhart et al.
4,561,110 A 12/1985 Herbert
4,564,054 A 1/1986 Gustavsson
4,568,331 A 2/1986 Fischer et al.
4,568,336 A 2/1986 Cooper
4,568,346 A 2/1986 van Dijk
4,573,967 A 3/1986 Hargrove et al.
4,573,993 A 3/1986 Hoag et al.
4,576,211 A 3/1986 Valentini et al.
4,579,553 A 4/1986 Urquhart et al.
4,581,016 A 4/1986 Gettig
4,583,971 A 4/1986 Bocquet et al.
4,583,981 A 4/1986 Urquhart et al.
4,586,922 A 5/1986 Theeuwes
4,589,867 A 5/1986 Israel
4,589,879 A 5/1986 Pearson
4,590,234 A 5/1986 Tasaka et al.
4,596,555 A 6/1986 Theeuwes
4,601,704 A 7/1986 Larkin
4,602,910 A 7/1986 Larkin
4,606,734 A 8/1986 Larkin et al.
4,607,671 A 8/1986 Aalto et al.
4,608,043 A 8/1986 Larkin
4,610,684 A 9/1986 Knox et al.
4,613,326 A 9/1986 Szwarc
4,614,267 A 9/1986 Larkin
4,614,515 A 9/1986 Tripp et al.
4,623,334 A 11/1986 Riddell
4,629,080 A 12/1986 Carveth
4,630,727 A 12/1986 Feriani et al.
4,632,244 A 12/1986 Landau
4,637,934 A 1/1987 White
4,650,475 A 3/1987 Smith et al.
4,662,878 A 5/1987 Lindmayer
4,664,650 A 5/1987 Urquhart et al.
4,668,219 A 5/1987 Israel
4,673,404 A 6/1987 Gustavsson
4,675,020 A 6/1987 McPhee
4,692,144 A 9/1987 Carpenter
4,693,706 A 9/1987 Ennis, III
4,695,272 A 9/1987 Berglund et al.
4,703,864 A 11/1987 Larkin et al.
4,715,854 A 12/1987 Vaillancourt
4,717,388 A 1/1988 Steer et al.
4,722,733 A 2/1988 Howson
4,723,956 A 2/1988 Schnell et al.
4,727,985 A 3/1988 McNeirney et al.
4,731,053 A 3/1988 Hoffman
4,735,608 A 4/1988 Sardam
4,740,103 A 4/1988 Theeuwes
4,740,197 A 4/1988 Theeuwes
4,740,198 A 4/1988 Theeuwes
4,740,199 A 4/1988 Theeuwes
4,740,200 A 4/1988 Theeuwes
4,740,201 A 4/1988 Theeuwes
4,741,734 A 5/1988 Theeuwes
4,741,735 A 5/1988 Theeuwes
4,743,229 A 5/1988 Chu
4,747,834 A 5/1988 Prindle
4,752,292 A 6/1988 Lopez et al.
4,757,911 A 7/1988 Larkin et al.
4,759,756 A 7/1988 Forman et al.
4,778,453 A 10/1988 Lopez
4,781,679 A 11/1988 Larkin
4,782,841 A 11/1988 Lopez
4,784,259 A 11/1988 Grabenkort
4,784,658 A 11/1988 Grabenkort
4,785,858 A 11/1988 Valentini et al.
4,786,279 A 11/1988 Wilkinson et al.
4,787,429 A 11/1988 Valentini et al.
4,790,820 A 12/1988 Theeuwes
4,804,360 A 2/1989 Kamen
4,804,366 A 2/1989 Zdeb et al.
4,808,381 A 2/1989 McGregor et al.
4,816,024 A 3/1989 Sitar et al.
4,819,659 A 4/1989 Sitar
4,820,269 A 4/1989 Riddell
4,822,351 A 4/1989 Purcell
4,832,690 A 5/1989 Kuu
4,834,149 A 5/1989 Fournier et al.

| | | | |
|---|---|---|---|
| 4,834,152 | A | 5/1989 | Howson et al. |
| 4,842,028 | A | 6/1989 | Kaufman et al. |
| 4,850,978 | A | 7/1989 | Dudar et al. |
| 4,857,052 | A | 8/1989 | Theeuwes |
| 4,861,335 | A | 8/1989 | Reynolds |
| 4,861,585 | A | 8/1989 | Galef, Jr. et al. |
| 4,865,354 | A | 9/1989 | Allen |
| 4,871,354 | A | 10/1989 | Conn et al. |
| 4,871,360 | A | 10/1989 | Theeuwes |
| 4,871,463 | A | 10/1989 | Taylor et al. |
| 4,872,494 | A | 10/1989 | Coccia |
| 4,874,366 | A | 10/1989 | Zdeb et al. |
| 4,874,368 | A | 10/1989 | Miller et al. |
| 4,883,483 | A | 11/1989 | Lindmayer |
| 4,886,495 | A | 12/1989 | Reynolds |
| 4,898,209 | A | 2/1990 | Zbed |
| 4,906,103 | A | 3/1990 | Kao |
| 4,908,019 | A | 3/1990 | Urquhart et al. |
| 4,909,290 | A | 3/1990 | Coccia |
| 4,911,708 | A | 3/1990 | Maezaki et al. |
| 4,915,689 | A | 4/1990 | Theeuwes |
| 4,927,013 | A | 5/1990 | Van Brunt et al. |
| 4,927,423 | A | 5/1990 | Malmborg |
| 4,927,605 | A | 5/1990 | Dorn et al. |
| 4,931,048 | A | 6/1990 | Lopez |
| 4,936,445 | A | 6/1990 | Grabenkort |
| 4,936,829 | A | 6/1990 | Zdeb et al. |
| 4,936,841 | A | 6/1990 | Aoki et al. |
| 4,944,736 | A | 7/1990 | Holtz |
| 4,948,000 | A | 8/1990 | Grabenkort |
| 4,950,237 | A | 8/1990 | Henault et al. |
| 4,961,495 | A | 10/1990 | Yoshida et al. |
| 4,968,299 | A | 11/1990 | Ahlstrand et al. |
| 4,969,883 | A | 11/1990 | Gilbert et al. |
| 4,973,307 | A | 11/1990 | Theeuwes |
| 4,978,337 | A | 12/1990 | Theeuwes |
| 4,979,942 | A | 12/1990 | Wolf et al. |
| 4,982,875 | A | 1/1991 | Pozzi et al. |
| 4,983,164 | A | 1/1991 | Hook et al. |
| 4,985,016 | A | 1/1991 | Theeuwes et al. |
| 4,986,322 | A | 1/1991 | Chibret et al. |
| 4,994,031 | A | 2/1991 | Theeuwes |
| 4,994,056 | A | 2/1991 | Ikeda |
| 4,996,579 | A | 2/1991 | Chu |
| 4,997,083 | A | 3/1991 | Loretti et al. |
| 4,997,430 | A | 3/1991 | Van der Heiden et al. |
| 5,002,530 | A | 3/1991 | Recker et al. |
| 5,023,119 | A | 6/1991 | Yamakoshi |
| 5,024,657 | A | 6/1991 | Needham et al. |
| 5,030,203 | A | 7/1991 | Wolf, Jr. et al. |
| 5,032,117 | A | 7/1991 | Motta |
| 5,045,081 | A | 9/1991 | Dysarz |
| 5,049,129 | A | 9/1991 | Zdeb et al. |
| 5,049,135 | A | 9/1991 | Davis |
| 5,061,264 | A | 10/1991 | Scarrow |
| 5,064,059 | A | 11/1991 | Ziegler et al. |
| 5,069,671 | A | 12/1991 | Theeuwes |
| 5,074,844 | A | 12/1991 | Zdeb et al. |
| 5,074,849 | A | 12/1991 | Sachse |
| D323,389 | S | 1/1992 | Aoki et al. |
| 5,080,652 | A | 1/1992 | Sancoff et al. |
| 5,084,040 | A | 1/1992 | Sutter |
| 5,088,996 | A | 2/1992 | Kopfer et al. |
| 5,100,394 | A | 3/1992 | Dudar et al. |
| 5,102,408 | A | 4/1992 | Hamacher |
| 5,104,375 | A | 4/1992 | Wolf et al. |
| 5,114,044 | A | 5/1992 | Isono et al. |
| 5,114,411 | A | 5/1992 | Haber et al. |
| 5,116,315 | A | 5/1992 | Capozzi et al. |
| 5,116,316 | A | 5/1992 | Sertic et al. |
| 5,117,875 | A | 6/1992 | Marrucchi |
| 5,122,123 | A | 6/1992 | Vaillancourt |
| 5,125,892 | A | 6/1992 | Drudik |
| 5,125,908 | A | 6/1992 | Cohen |
| 5,126,175 | A | 6/1992 | Yamakoshi |
| 5,129,894 | A | 7/1992 | Sommermeyer et al. |
| 5,137,511 | A | 8/1992 | Reynolds |
| 5,147,324 | A | 9/1992 | Skakoon et al. |
| 5,152,965 | A | 10/1992 | Fisk et al. |
| 5,156,598 | A | 10/1992 | Skakoon et al. |
| 5,158,546 | A | 10/1992 | Haber et al. |
| 5,160,320 | A | 11/1992 | Yum et al. |
| 5,167,642 | A | 12/1992 | Fowles |
| 5,169,388 | A | 12/1992 | McPhee |
| 5,171,214 | A | 12/1992 | Kolber et al. |
| 5,171,219 | A | 12/1992 | Fujioka et al. |
| 5,171,220 | A | 12/1992 | Morimoto |
| 5,176,634 | A | 1/1993 | Smith et al. |
| 5,176,673 | A | 1/1993 | Marrucchi |
| 5,181,909 | A | 1/1993 | McFarlane |
| 5,186,323 | A | 2/1993 | Pfleger |
| 5,188,615 | A | 2/1993 | Haber et al. |
| 5,188,629 | A | 2/1993 | Shimoda |
| 5,195,658 | A | 3/1993 | Hoshino |
| 5,195,986 | A | 3/1993 | Kamen |
| 5,196,001 | A | 3/1993 | Kao |
| 5,199,947 | A | 4/1993 | Lopez et al. |
| 5,199,948 | A | 4/1993 | McPhee |
| 5,200,200 | A | 4/1993 | Veech |
| 5,201,705 | A | 4/1993 | Berglund et al. |
| 5,207,509 | A | 5/1993 | Herbert |
| 5,209,201 | A | 5/1993 | Horie et al. |
| 5,209,347 | A | 5/1993 | Fabisiewicz et al. |
| 5,211,201 | A | 5/1993 | Kamen et al. |
| 5,211,285 | A | 5/1993 | Haber et al. |
| 5,222,946 | A | 6/1993 | Kamen |
| 5,226,878 | A | 7/1993 | Young |
| 5,226,900 | A | 7/1993 | Bancsi et al. |
| RE34,365 | E | 8/1993 | Theeuwes |
| 5,232,029 | A | 8/1993 | Knox et al. |
| 5,232,109 | A | 8/1993 | Tirrell et al. |
| 5,246,142 | A | 9/1993 | DiPalma et al. |
| 5,247,972 | A | 9/1993 | Tetreault |
| 5,250,028 | A | 10/1993 | Theeuwes et al. |
| 5,257,985 | A | 11/1993 | Puhl |
| 5,257,986 | A | 11/1993 | Herbert et al. |
| 5,257,987 | A | 11/1993 | Athayde et al. |
| 5,259,843 | A | 11/1993 | Watanabe et al. |
| 5,259,954 | A | 11/1993 | Taylor |
| 5,261,902 | A | 11/1993 | Okada et al. |
| 5,267,646 | A | 12/1993 | Inoue et al. |
| 5,267,957 | A | 12/1993 | Kriesel et al. |
| 5,279,576 | A | 1/1994 | Loo et al. |
| 5,279,579 | A | 1/1994 | D'Amico |
| 5,279,583 | A | 1/1994 | Shober, Jr. et al. |
| 5,281,198 | A | 1/1994 | Haber et al. |
| 5,281,206 | A | 1/1994 | Lopez |
| 5,286,257 | A | 2/1994 | Fischer |
| 5,287,961 | A | 2/1994 | Herran |
| 5,289,585 | A | 2/1994 | Kock et al. |
| 5,302,603 | A | 4/1994 | Crawley et al. |
| 5,303,751 | A | 4/1994 | Slater et al. |
| 5,304,130 | A | 4/1994 | Button et al. |
| 5,304,163 | A | 4/1994 | Bonnici et al. |
| 5,304,165 | A | 4/1994 | Haber et al. |
| 5,306,242 | A | 4/1994 | Joyce et al. |
| 5,308,287 | A | 5/1994 | Gunsing |
| 5,308,347 | A | 5/1994 | Sunago et al. |
| 5,320,603 | A | 6/1994 | Vetter et al. |
| 5,328,464 | A | 7/1994 | Kriesel et al. |
| 5,330,048 | A | 7/1994 | Haber et al. |
| 5,330,426 | A | 7/1994 | Kriesel et al. |

5,330,450 A 7/1994 Lopez
5,330,462 A 7/1994 Nakamura
5,330,464 A 7/1994 Mathias et al.
5,332,399 A 7/1994 Grabenkort et al.
5,334,178 A 8/1994 Haber et al.
5,334,180 A 8/1994 Adolf et al.
5,334,188 A 8/1994 Inoue et al.
5,335,773 A 8/1994 Haber et al.
5,336,180 A 8/1994 Kriesel et al.
5,342,346 A 8/1994 Honda et al.
5,342,347 A 8/1994 Kikuchi et al.
5,344,414 A 9/1994 Lopez et al.
5,348,060 A 9/1994 Futagawa et al.
5,348,600 A 9/1994 Ishii
5,350,372 A 9/1994 Ikeda et al.
5,350,546 A 9/1994 Takeuchi et al.
5,352,191 A 10/1994 Sunago et al.
5,352,196 A 10/1994 Haber et al.
5,352,210 A 10/1994 Marrucchi
5,353,961 A 10/1994 Debush
5,356,380 A 10/1994 Hoekwater et al.
5,358,501 A 10/1994 Meyer
5,360,410 A 11/1994 Wacks
5,364,350 A 11/1994 Dittmann
5,364,369 A 11/1994 Reynolds
5,364,371 A 11/1994 Kamen
5,364,384 A 11/1994 Grabenkort et al.
5,368,586 A 11/1994 Van Der Heiden et al.
5,370,164 A 12/1994 Galloway
5,373,966 A 12/1994 O'Reilly et al.
5,374,264 A 12/1994 Wadsworth, Jr.
5,376,079 A 12/1994 Holm
5,380,281 A 1/1995 Tomellini et al.
5,380,315 A 1/1995 Isono et al.
5,385,545 A 1/1995 Kriesel et al.
5,385,546 A 1/1995 Kriesel et al.
5,385,547 A 1/1995 Wong et al.
5,386,372 A 1/1995 Kobayashi et al.
5,393,497 A 2/1995 Haber et al.
5,397,303 A 3/1995 Sancoff et al.
5,398,851 A 3/1995 Sancoff et al.
5,401,253 A 3/1995 Reynolds
5,409,141 A 4/1995 Kikuchi et al.
5,423,421 A 6/1995 Inoue et al.
5,423,753 A 6/1995 Fowles et al.
5,423,793 A 6/1995 Isono et al.
5,423,796 A 6/1995 Shikhman et al.
5,425,447 A 6/1995 Farina
5,425,528 A 6/1995 Rains et al.
5,429,256 A 7/1995 Kestenbaum
5,429,603 A 7/1995 Morris
5,429,614 A 7/1995 Fowles et al.
5,435,076 A 7/1995 Hjertman et al.
5,445,631 A 8/1995 Uchida
5,458,593 A 10/1995 Macabasco et al.
5,462,526 A 10/1995 Barney et al.
5,464,123 A 11/1995 Scarrow
5,470,327 A 11/1995 Helgren et al.
5,472,022 A 12/1995 Michel et al.
5,472,422 A 12/1995 Ljungquist
5,474,540 A 12/1995 Miller et al.
5,478,337 A 12/1995 Okamoto et al.
5,484,406 A 1/1996 Wong et al.
5,484,410 A 1/1996 Kriesel et al.
5,489,266 A 2/1996 Grimard
5,490,848 A 2/1996 Finley et al.
5,492,147 A 2/1996 Challender et al.
5,492,219 A 2/1996 Stupar
5,493,774 A 2/1996 Grabenkort
5,494,190 A 2/1996 Boettcher
5,501,887 A 3/1996 Tanaka et al.
5,509,898 A 4/1996 Isono et al.
5,510,115 A 4/1996 Breillatt, Jr. et al.
5,514,090 A 5/1996 Kriesel et al.
5,520,972 A 5/1996 Ezaki et al.
5,522,804 A 6/1996 Lynn
5,526,853 A 6/1996 McPhee et al.
5,531,683 A 7/1996 Kriesel et al.
5,533,389 A 7/1996 Kamen et al.
5,533,973 A 7/1996 Piontek et al.
5,533,994 A 7/1996 Meyer
5,535,746 A 7/1996 Hoover et al.
5,536,469 A 7/1996 Jonsson et al.
5,538,506 A 7/1996 Farris et al.
5,540,674 A 7/1996 Karas et al.
5,547,471 A 8/1996 Thompson et al.
5,554,125 A 9/1996 Reynolds
5,554,128 A 9/1996 Hedges
5,560,403 A 10/1996 Balteau et al.
5,566,729 A 10/1996 Grabenkort et al.
5,569,191 A 10/1996 Meyer
5,569,192 A 10/1996 van der Wal
5,573,527 A 11/1996 Macabasco et al.
5,575,310 A 11/1996 Kamen et al.
5,577,369 A 11/1996 Becker et al.
5,584,808 A 12/1996 Healy
5,593,028 A 1/1997 Haber et al.
5,595,314 A 1/1997 Weiler
5,596,193 A 1/1997 Chutjian et al.
5,603,695 A 2/1997 Erickson
5,603,696 A 2/1997 Williams et al.
5,605,542 A 2/1997 Tanaka et al.
5,611,792 A 3/1997 Gustafsson
5,620,434 A 4/1997 Brony
5,624,405 A 4/1997 Futagawa et al.
5,641,010 A 6/1997 Maier
5,688,254 A 11/1997 Lopez et al.
5,709,666 A 1/1998 Reynolds
5,827,262 A 10/1998 Neftel et al.
5,897,526 A 4/1999 Vaillancourt
5,989,237 A 11/1999 Fowles et al.
6,019,750 A 2/2000 Fowles et al.
6,071,270 A * 6/2000 Fowles et al. ......... 137/614.04
6,090,092 A * 7/2000 Fowles et al. .............. 604/413
6,378,714 B1 * 4/2002 Jansen et al. ............... 141/329

FOREIGN PATENT DOCUMENTS

GB 2 211 104 A 6/1989
WO WO 83/03540 10/1983
WO WO 85/03432 8/1985
WO WO 90/03536 4/1990
WO WO 92/11897 7/1992
WO WO 93/02723 2/1993
WO WO 93/09825 5/1993
WO WO 97/25015 7/1997

* cited by examiner

SLIDING RECONSTITUTION DEVICE WITH SEAL

This is a continuation of application Ser. No. 08/986,580, filed Dec. 4, 1997 now U.S. Pat. No. 6,071,270, which is incorporated herein by reference and made a part hereof, and upon which a claim of priority is based.

TECHNICAL FIELD

The present invention relates generally to the delivery of a beneficial agent to a patient. More specifically, the present invention relates to an improved device for reconstituting a beneficial agent to be delivered to a patient.

BACKGROUND OF THE INVENTION

Many drugs are unstable even for a short period of time in a dissolved state and therefore are packaged, stored, and shipped in a powdered or lyophilized state to increase their shelf life. In order for powdered drugs to be given intravenously to a patient, the drugs must first be placed in liquid form. To this end, these drugs are mixed or reconstituted with a diluent before being delivered intravenously to a patient. The diluents may be, for example, a dextrose solution, a saline solution, or even water. Typically the drugs are stored in powdered form in glass vials or ampules.

Other drugs, although in a liquid state, must still be diluted before administering to a patient. For example, some chemotherapy drugs are stored in glass vials or ampules, in a liquid state, but must be diluted prior to use. As used herein, reconstitution means to place the powdered drug in a drug already in liquid form, as well as, to further dilute a liquid drug.

Many companies that manufacture the drug do not make the diluent, and vice versa; therefore, the lyophilized drug and the diluent are sold separately. It is necessary for the doctor, pharmacist, nurse, or other medical personnel to mix the drug with diluent prior to use. Reconstituting the drug presents a number of problems. The reconstitution procedure is time consuming and requires aseptic technique. Further, the proper drug and diluent must be utilized or the product must be disposed of.

The reconstitution procedure should be performed under sterile conditions. In some procedures for reconstituting, maintaining sterile conditions is difficult. Moreover, some drugs, such as chemotherapy drugs, are toxic and exposure to the medical personnel during the reconstitution procedure can be dangerous. One way of reconstituting a powdered drug is to inject the liquid diluent directly into the drug vial. This can be performed by use of a combination-syringe and syringe needle having diluent therein. In this regard, drug vials typically include a pierceable rubber stopper. The rubber stopper of the drug vial is pierced by the needle, and liquid in the syringe is then injected into the vial. The vial is shaken to mix the powdered drug with the liquid. After the liquid and drug are mixed, a measured amount of the reconstituted drug is then drawn into the syringe. The syringe is then withdrawn from the vial and the drug can then be injected into the patient. Another method of drug administration is to inject the reconstituted drug, contained in the syringe, into a parenteral solution container. Examples of such containers include the MINI-BAG™ flexible parenteral solution container or VIAFLEX® flexible parenteral solution container sold by Baxter Healthcare corporation of Deerfield, Ill. These parenteral solution containers may already have therein dextrose or saline solutions. The reconstituted drug is injected into the container, mixed with the solution in the parenteral solution container and delivered through an intravenous solution administration set to a vein access site of the patient.

Another method for reconstituting a powdered drug utilizes a reconstitution device sold by Baxter Healthcare Corporation, product code No. 2B8064. That device includes a double pointed needle and guide tubes mounted around both ends of the needle. This reconstitution device is utilized to place the drug vial in flow communication with a flexible-walled parenteral solution container. Once the connection is made by piercing a port of the flexible container with one end of the needle and the vial stopper with the other end of the needle, liquid in the solution container may be forced through the needle into the drug vial by squeezing the sidewalls of the solution container. The vial is then shaken to mix the liquid and drug. The liquid in the vial is withdrawn by squeezing air from the solution container into the vial. When compression of the flexible walled solution container is stopped, the pressurized air in the vial acts as a pump to force the liquid in the vial back into the solution container.

An improvement to this product is the subject of commonly assigned U.S. Pat. No. 4,607,671 to Aalto et al. The device of that invention includes a series of bumps on the inside of a sheath to grip a drug vial. These bumps hinder the inadvertent disconnection of the device with the vial.

U.S. Pat. No. 4,759,756 discloses a reconstitution device which, in an embodiment, includes an improved vial adaptor and bag adaptor that permit the permanent coupling of a vial and liquid container. The bag adaptor is rotatable relative to the vial adaptor to either block fluid communication in a first position or effect fluid communication in a second position.

Another form of reconstitution device is seen in commonly assigned U.S. Pat. No. 3,976,073 to Quick et al. Yet another type of reconstitution device is disclosed in U.S. Pat. No. 4,328,802 to Curley et al., entitled “Wet-Dry Syringe Package” which includes a vial adaptor having inwardly directed retaining projections to firmly grip the retaining cap lip of a drug vial to secure the vial to the vial adaptor. The package disclosed by Curley et al. is directed to reconstituting a drug by use of a liquid-filled syringe.

Other methods for reconstituting a drug are shown, for example, in commonly assigned U.S. Pat. No. 4,410,321 to Pearson et al., entitled “Close Drug Delivery System”; U.S. Pat. Nos. 4,411,662 and 4,432,755 to Pearson, both entitled “Sterile Coupling”; U.S. Pat. No. 4,458,733 to Lyons entitled “Mixing Apparatus”; and U.S. Pat. No. 4,898,209 to Zdeb entitled “Sliding Reconstitution Device With Seal.”

Other related patents include U.S. Pat. No. 4,872,867 to Kilinger entitled “Wet-Dry Additive Assembly”; U.S. Pat. No. 3,841,329 to Kilinger entitled “Compact Syringe”; U.S. Pat. No. 3,826,261 to Kilinger entitled “Vial and Syringe Assembly”; U.S. Pat. No. 3,826,260 to Kilinger entitled “Vial and Syringe Combination”; U.S. Pat. No. 3,378,369 to Kilinger entitled “Apparatus for Transferring Liquid Between a Container and a Flexible Bag”; and German specification DE OS 36 27 231.

Commonly assigned U.S. Pat. No. 4,898,209 to Zdeb (the ’209 patent), discloses a sliding reconstitution device which solved some of the problems associated with conventional reconstitution systems. (See FIG. 1). As can be seen in FIG. 1, the ’209 patent discloses a first sleeve member that is mounted concentrically about a second sleeve member. The sleeve members can be moved axially with respect to each other to cause a needle or cannula to pierce a drug container and a diluent container to place the containers in fluid communication with each other. The process for using the '209 connector requires three distinct steps. The sleeves have to be rotated with respect to one another to move the device into an unlocked position. The sleeves are then moved axially with respect to one another to an activated position to pierce closures of the containers. The sleeves are rotated again, in a direction opposite of that direction taken in the first step, to lock the sleeves in the activated position.

The connector described in the '209 patent allowed for preattaching the device to a vial without piercing a closure of the vial. However, no seal was provided on the opposite end of the connector, so the vial and device assembly had to be used relatively quickly after connection or stored in a sterile environment, such as under a hood. Also, the '209 patent does not disclose any structure for preventing the device from becoming inadvertently disassembled when being moved to the activated position. The second sleeve is capable of sliding entirely through the first sleeve member and becoming disassociated from the first sleeve member. This would require the medical personnel to either reassemble the device, or, potentially, dispose of it due to contamination.

The device described in the '209 patent, also does not provide a visual indication that the device is in the activated position. It is also possible for the device described in the '209 patent to be inadvertently moved to the inactivated position, by merely rotating the first and second sleeve members in a direction opposite of that taken in the third step described above.

Additionally, it was possible for the second container, which is frequently a vial, to rotate within the device. This could cause coring of the vial stopper which could lead to leakage of the vial stopper. Additionally it was possible for a vial to be misaligned while being attached to the device, causing the attachment process to be difficult for medical personnel. Further, the connector could be relatively easily removed from the vial. Removal of the vial could remove all evidence that the reconstitution step had occurred and, possibly, lead to a second unintended dosage of medicine being administered. Finally, the seal had a sleeve that covered only a portion of the cannula. The sleeve of the seal was relatively resilient and had the tendency to push the connector away from the drug container when docked thereto and activated.

Yet another connector for attaching a drug vial to a parenteral solution container is disclosed in U.S. Pat. No. 4,675,020. The '020 patent discloses a connector having an end that docks to a drug vial and an opposite end that connects to the solution container. A shoulder and an end surface of the vial are held between first and second jaws of the vial end of the connector. The second jaws 71 terminate in a relatively sharp point that digs into and deforms the outermost end surface 94 of the vial sufficiently to accommodate dimensional variations between the shoulder and the outermost end surface of the vial. The marks that are left in the deformable end surface of the vial are intended to provide a tamper evident indication. However, tamper evident marks may not be left in vials that have a cap that is too short to impinge upon the sharp points.

The connector disclosed in the '020 patent has a spike 25 that penetrates stoppers on the vial and on the solution container to place these containers in fluid communication. However, because the spike 25 extends outwardly beyond skirt sections 57, the '020 connector cannot be preattached to the fluid container or the drug container without piercing the stoppers of each. This is undesirable, as it initiates the time period in which the drug must be used, and typically this is a shorter period relative to the normal shelf-life of the drug product. (The '020 patent states that the connector may be preassembled onto a drug vial (Col. 6, lines 40–49), but there is no detailed description of a structure that would allow such pre-assembly).

The '020 device also does not provide a structure for preventing a docked vial from rotating relative to the spike 25. A closure of the vial can become damaged or cored upon rotation, which in turn, can lead to particles from the closure from entering the fluid that eventually passes to a patient. It can also lead to leakage of the closure of the vial.

SUMMARY OF THE INVENTION

The present invention provides a fluid reconstitution device. To this end, there is provided a device having a first sleeve member and a second sleeve member which are operatively engaged so that the first sleeve can slide axially relative to the second sleeve member. At one end of the first sleeve there is included a means for connecting the sleeve to a first container of diluent, for example a flexible parenteral bag. The second sleeve member is adapted at an end opposite the first container to connect to a second container of a beneficial agent, such as a standard drug vial. The beneficial agent may be a drug in liquid or lyophilized form. A piercing member is provided within one of the first and second sleeve members. Preferably the piercing member is a double-ended cannula for accessing both the first and second containers and to establish fluid communication therebetween.

The device is movable between an inactivated position and an activated position. When in the second activated position the first and second containers are punctured by the piercing member, placing them in fluid communication so the drug and the diluent may be mixed.

The second sleeve member further includes means for sealing an end of the second sleeve member to the second container. Preferably, the seal is an elastomeric disk-shaped septum having an axially extending resilient sleeve member that is dimensioned to fit about the piercing member to protect it from contamination. In a more preferred embodiment, the septum also includes a centrally disposed, axially extending annular ridge that is dimensioned to form a fluid-tight seal with an aperture of the second container.

In an embodiment, the coupling device includes a means for preventing the device from inadvertently moving from the activated position to the inactivated position. In a more preferred embodiment, the means for locking is a deformable protuberance on one of the sleeve members which causes an interference fit between the first and second sleeve members.

In another embodiment of the device, there is included a barrier which covers the proximal end of the first sleeve member. In the presently preferred embodiment, the barrier is a thin metal film which overlays the opening of the first sleeve member to protect the cannula from contamination during handling. It is also possible to use a polymeric based barrier such as TYVEK®, or paper and the like.

In another embodiment, the coupling device includes a plurality of circumferentially spaced and axially extending segmented fingers located on the proximal end of the second sleeve member that are adapted to engage the second container. In a more preferred embodiment, the fingers include a flat lead-in section which guide the fingers over an end of the second container to assist in connecting the device to the second container. The fingers further include a tapered section extending from the lead-in section which terminate to form a buttress for firmly engaging the second container. When the second container is a drug vial, the connector may be docked to the drug vial without piercing a stopper of the vial. This is signficant because piercing the stopper of the vial starts the docked dating time period. Because simply attaching the connector to the vial does not result in a piercing of the vial stopper, the connector can be connected to the vial for a period equivalent to the vial expiration period.

In another embodiment, the coupling device includes a means for visually indicating that the coupling device is in the activated position. In the most preferred embodiment, the means is a color indication system whereby portions of the first sleeve member, which are not visible when in the activated position, are a different color than portions of the first sleeve member that are visible when in the activated position. Thus, in the inactivated position one can see two different colors, but in the activated position only one color is visible.

In another embodiment, the coupling device includes a means for preventing the first sleeve member from becoming disassociated from the second sleeve member. In a more preferred embodiment, the second sleeve member forms a channel for the first sleeve member and slidingly receives the first sleeve member. A bushing having a diameter greater than that of the second sleeve member is connected to the proximal end of the first sleeve member, preventing it from becoming disassociated when being moved from the inactivated position to the activated position.

DETAILED DESCRIPTION OF THE PREFERRED EMBODIMENTS

Figure 1:
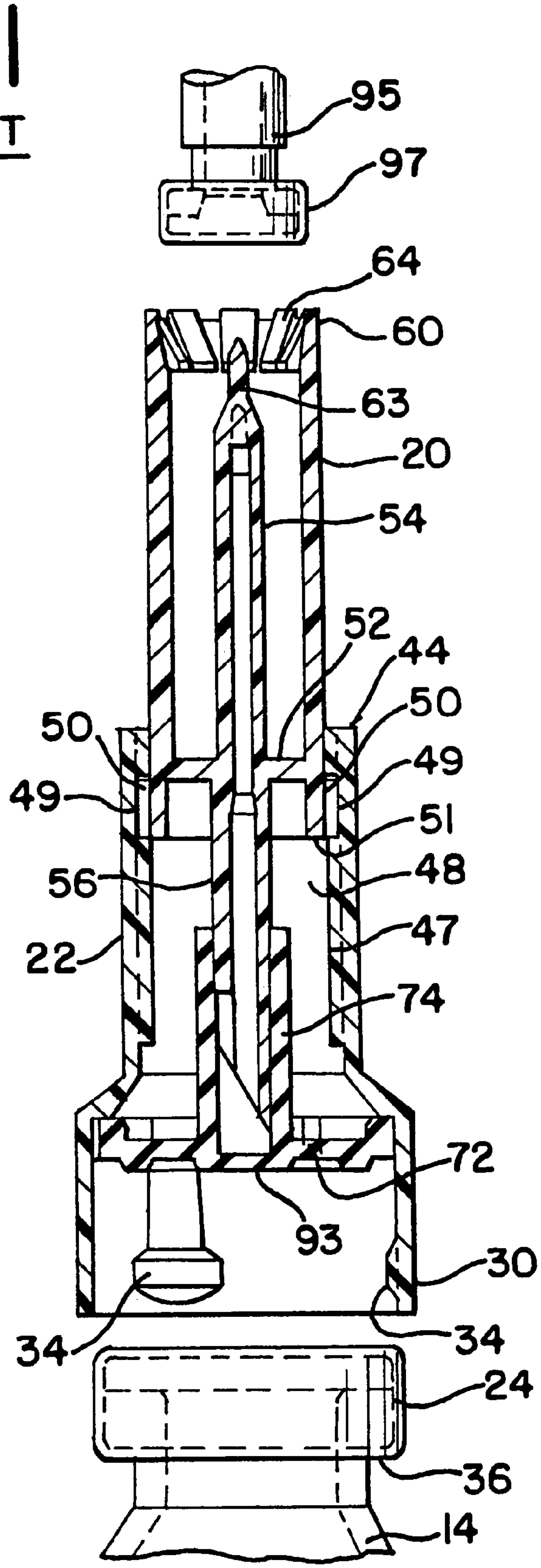
FIG. 1 PRIOR ART
FIG. 1 is a figure selected from U.S. Pat. No. 4,889,209, including its reference numerals.

While the invention is susceptible of embodiment in many different forms, there is shown in the drawings and will herein be described in detail a preferred embodiment of the invention. It is to be understood that the present disclosure is to be considered as an exemplification of the principles of the invention. This disclosure is not intended to limit the broad aspect of the invention to the illustrated embodiments.

The present invention provides a connector device that is used to mix two substances within separate containers. More particularly, the invention provides a device to reconstitute a drug with a diluent. To accomplish the reconstitution of the drug, the invention provides an improved apparatus for attaching to a first container, commonly a flexible bag, containing a diluent, to a second container, commonly a vial containing a drug to be reconstituted. The connector provides fluid communication between the two containers so that the drug may be reconstituted, and delivered to a patient. While the diluent will be a liquid, the beneficial agent may be either a powder or a lyophilized drug to be dissolved or a liquid drug to be reduced in concentration.

Figure 2:
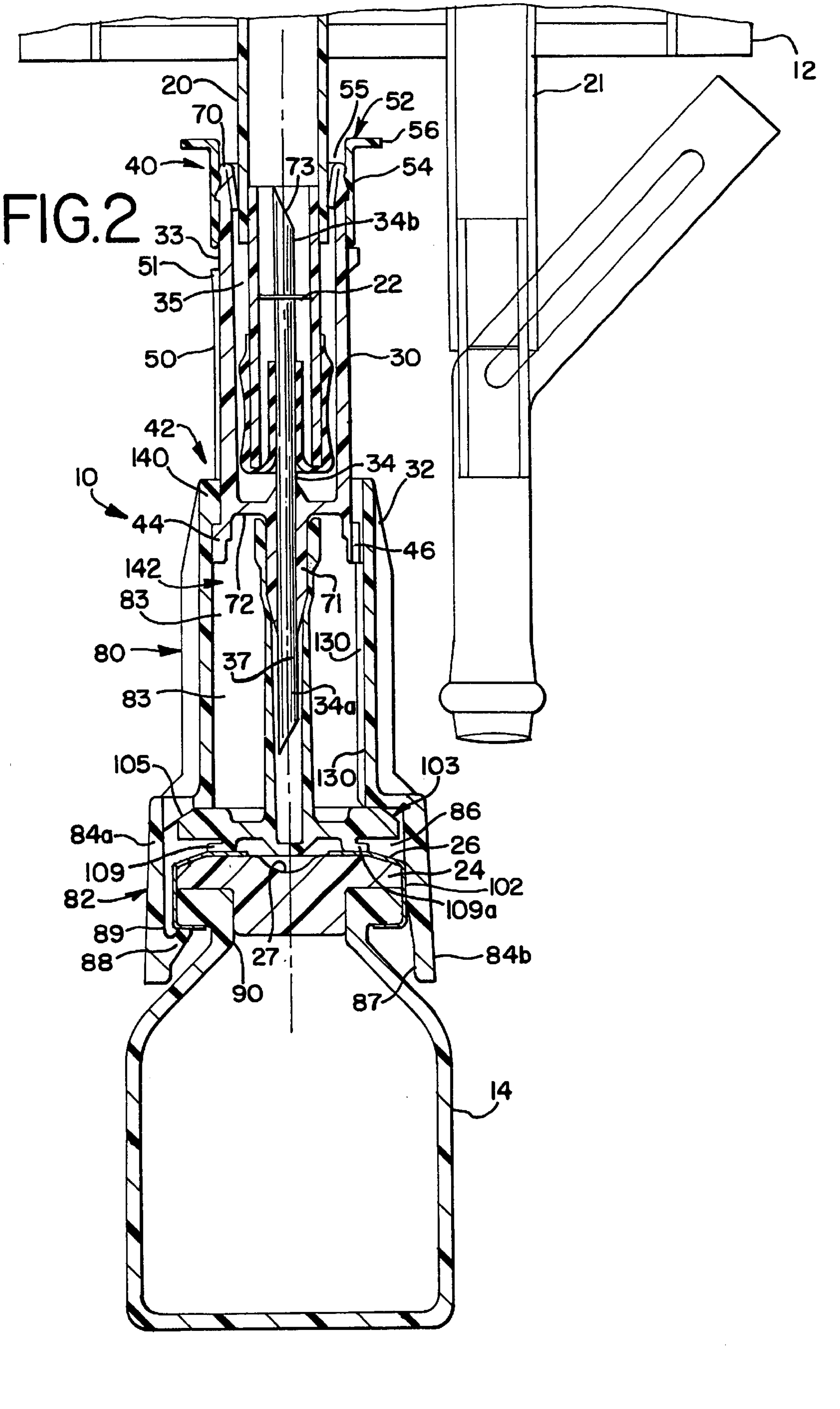
FIG. 2 is a elevational view in partial cross section of a reconstitution device of the present invention docked to a drug vial and parenteral container and in the inactivated position.

Referring to FIG. 2, a connector device 10 of the present invention is illustrated. The device 10 is adapted to place a first container 12 containing a liquid to be used as a diluent in fluid communication with a second container 14 containing a drug to be diluted or reconstituted. Prior to use, the device has means for independently hermetically sealing opposite ends of the device.

The first container 12 is a flexible bag as is typically used to contain solutions for a patient to be received intravenously. Flexible containers are typically constructed from two sheets of a polymeric material that are attached at their outer periphery to define a fluid tight chamber therebetween. At one point on the periphery of the container 12, a tubular port 20 is inserted between the sidewalls to provide access to the fluid chamber. The port 20 is typically sealed at a distal end with an elastomeric septum 22 or closure. A second port 21 is shown for allowing access by a fluid administration set to deliver the reconstituted drug to a patient. However, the first container 12 could be any container suitable for containing a liquid to be used to reconstitute a drug.

The second container 14, which contains a drug to be reconstituted, is a vial. The vial 14 is typically a glass container with a rubber stopper 24 inserted in an opening of the vial 14. The rubber stopper 24 is held in place by an apertured crimp ring 26 made of a soft metal, such as aluminum, that is crimped around the stopper 24 and the neck of the vial to fixedly attach it to the vial 14. Centrally located within the aperture is a target site 27 through which a needle or cannula passes to access the stopper of the vial. The device 10. can be adapted to accept vials of any size, particularly 20 mm and 13 mm vials. Additionally, the second container 14 could be any container that is adapted to accommodate drugs that require reconstitution.

Figure 3:
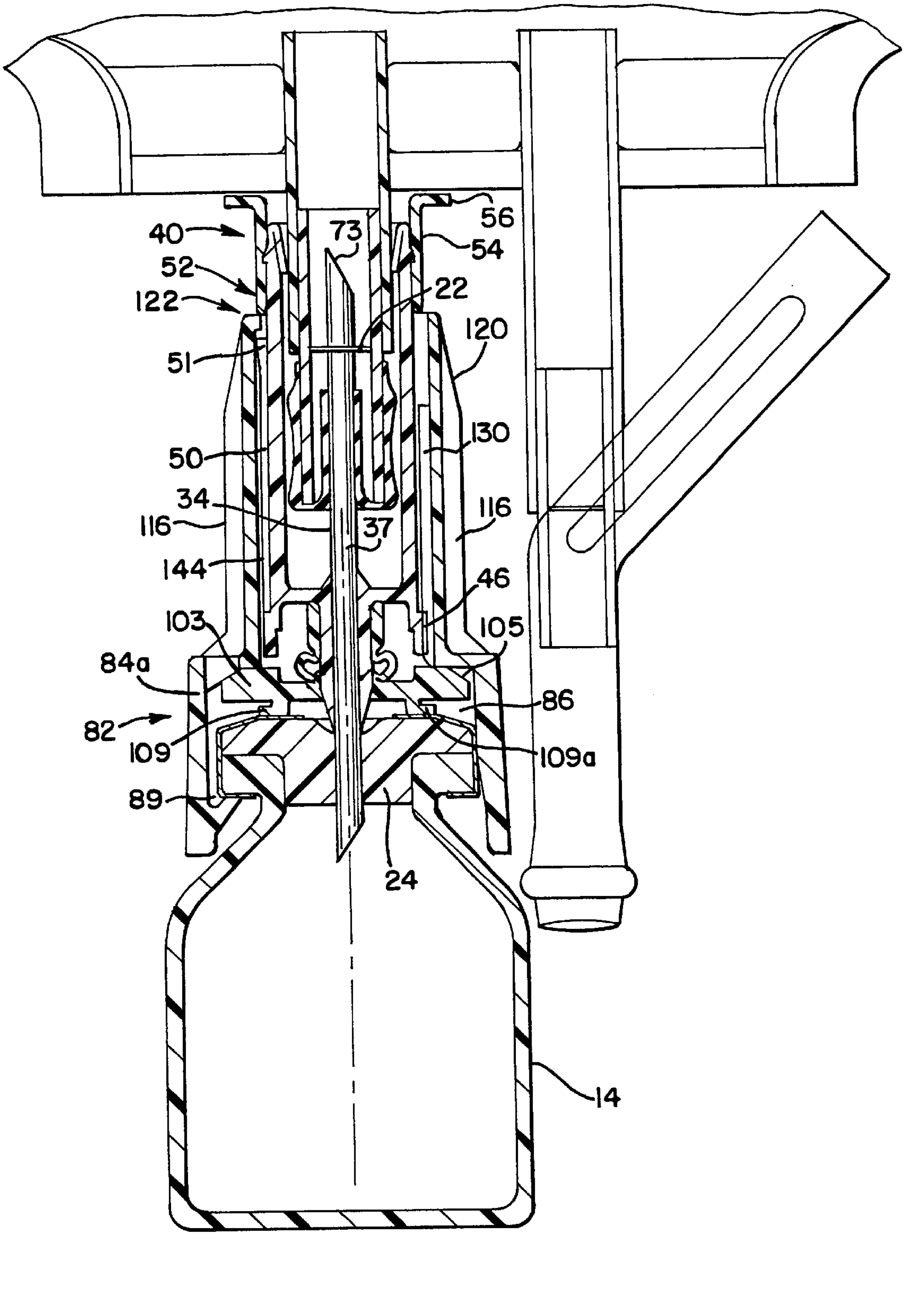
FIG. 3 is a partial cross-sectional view of the connector device of FIG. 2 showing the connector in an activated position.

The connector 10, as stated above, is adapted to connect to both the flexible bag 12 and the vial 14 and place the contents of the flexible bag 12 and the vial 14 into fluid communication with one another. The connector device 10 has first and second sleeve members 30 and 32. The first sleeve member 30 is associated with the second sleeve member 32 for relative axial movement from an inactivated position (FIG. 2) to an activated position (FIG. 3). What is meant by the activated position is that a piercing member 34 of the connector 10 is penetrating the stopper of the vial in a manner which places the flow channel of the piercing member in communication with the enclosed volume of the vial. What is meant by the inactivated position is that the piercing member 34 of the connector 10 is not penetrating the stopper of the vial in a manner which places the flow channel of the piercing member in communication with the enclosed volume of the vial. While FIG. 3 shows the connector 10 attached to a flexible bag 12, it should be understood that it is not necessary for the connector 10 to be connected to a flexible bag 12 to be either in the inactivated or the activated position. Preferably, the first and second sleeve members are made using standard injection molding techniques, although it will be understood that other fabrication techniques may be employed. In a preferred embodiment, the first and second sleeves 30 and 32 are made of a rigid yet deformable polymeric material such as a polycarbonate, polyester, polyolefin, or combinations of the same or the like.

Figure 4:
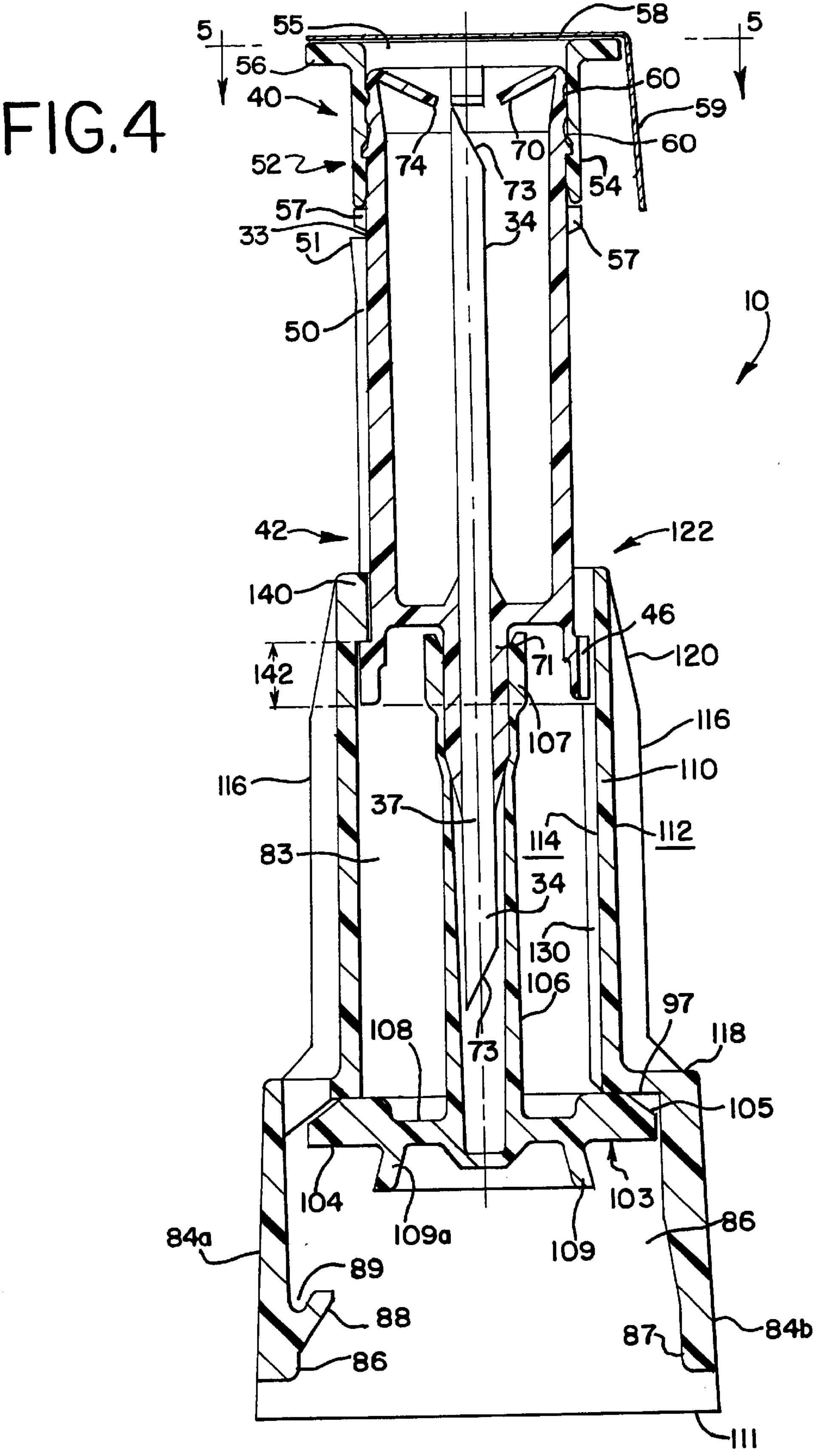
FIG. 4 is a cross-sectional view of the connector device of FIG. 2 not docked to a parenteral or drug container.

The first inactivated position, as shown in FIG. 2, allows for docking the connector 10 to both the flexible container 12 and the vial 14 without piercing the sealing member 24 of the vial 14. In the activated position, as shown in FIG. 4, a piercing member 34, such as a cannula or needle, has pierced the closures 22 and 24 of both containers 12, and 14 establishing fluid communication therebetween for reconstituting a drug contained in the vial 14.

Referring to FIGS. 2–4 and 9, means are provided for slidably mounting the first sleeve member 30 and the second sleeve member and more preferably the first sleeve member 30 is slidingly mounted within the second sleeve member 32 for relative axial and rotational movement therein. The first sleeve member 30 has a generally cylindrical wall 33 that defines a central channel 35 for receiving a portion of the piercing member 34. The piercing member has a central fluid passage 37 to establish a fluid flow path between the first and second containers 12 and 14. The first sleeve 30 has a first end 40 for connecting to the container 12 and a second end 42 for holding the piercing member 34. The second end 42 terminates in a first flange 44 that has a greater diameter than that of the cylindrical wall 33.

Two circumferentially spaced activation grooves 46 are provided on the outer surface 33 of the first sleeve 30 and extend across the first flange 44 and terminate at an intermediate portion of the cylindrical wall 33. Preferably the activation grooves 46 are spaced about 180 degrees apart and have a generally square-shaped cross section. As will be described below, the activation grooves 46 accommodate ribs positioned on an interior surface of the second sleeve 32 to allow for relative axial movement of the first and second sleeves 30 and 32 when the ribs and grooves are brought into alignment.

The first sleeve 30 further includes two circumferentially spaced axial locking ribs 50 that extend axially from a top of the first flange 44 and terminate short of the first end 40 of the first sleeve 30. The axial ribs 50 are each preferably positioned 90 degrees from the activation grooves 46. The device also includes means for locking the device in the activated position. To this end, the axial ribs 50 have an enlarged end portion 51 that, as will be described below, assist in locking the connector 10 in an activated position.

A bushing 52 is provided at the first end 40 of the first sleeve 30. The bushing 52 has a bushing sleeve 54, an aperture 55, a flange 56 circumjacent the aperture 55, and a foil closure 58. (FIG. 4). The bushing sleeve 54 slides over the cylindrical wall 33 and forms an interference fit therewith. A stop 57 is provided on the first sleeve 30 to abut an end of the bushing sleeve 54. The stop 57 includes several circumferentially spaced bumps. Preferably, the bushing sleeve 54 has an interior surface having two axially spaced annular ribs or ridges 60 (FIG. 4),that provide a hermetic seal with the cylindrical wall 33. The flange 56, as will be explained below, acts as a means for stopping the first and second sleeve members 30 and 32 from becoming disassociated from one another when the. connector is in the activated position and also provides a hand-hold for moving first and second sleeves 30 and 32 axially with respect to one another. The means for stopping could be another structure such as a ring or washer associated with the first or second sleeve members 30 and 32 to prevent them from sliding apart.

The foil seal 58 preferably is heat sealed to the bushing 52 and is releasably attached thereto so that it can be peeled away by pulling tear tab 59. It is contemplated by the present invention that the seal could be made of aluminum foil or of a polymeric based material such a TYVEK®, or spun paper or other material that is capable of being peelably attached to the bushing and capable of providing a barrier to the ingress of contaminants. It is also contemplated that sealing can be accomplished through induction welding or other sealing techniques. In preferred embodiments, the edges engaging the port tube are relatively sharp to more securely grip the port tube. As will be described below, the second sleeve member 32 has a separate hermetic seal such that the device is independently hermetically sealed at opposite ends.

Preferably the bushing is made of a low melting temperature material such as polyethylene or the like.

The first end 40 of the first sleeve member 30 has means for attaching to the first container or a first attaching member. In a preferred form, the means includes eight inwardly and downwardly extending resilient tabs 70. The tabs 70 fold inward and downward when the connector 10 is docked to port tube 20. The collective force of the tabs attempting to spring back to their original outwardly-extending position secures the connector 10 to the port tube 20 such that it cannot be detached without using a force considerably in excess of that normally used to operate the device. Such a force likely would break, detach or noticeably deform one or more of the tabs 70 or other portions of the connector in the process. Thus, the means fixedly attaches the connector to the first container. Though the present device utilizes eight tabs 70, it can be appreciated by one of reasonable skill in the art that more or fewer tabs could be utilized without departing from the scope of the present invention.

At the second end 42 of the first sleeve 30 is provided a generally concentrically mounted hub 71. The hub 71 extends from a bottom wall 72 of the first sleeve member 30. A portion of the piercing member **34*a* is for piercing the vial stopper 24 and a portion 34*b*, disposed in the central chamber 35, is for piercing the septum 22 of the container 12. The hub 71 is hermetically sealed to the piercing member 34** and has a lead-in section for guiding an enlarged end of the septum over the hub during assembly.

In the presently preferred embodiment, the piercing member 34 is a metal cannula that has oblique angles or bevels 73 on each end. It is also possible to fabricate the cannula 34 from a plastic material. For a plastic cannula, it is possible to fabricate the cannula 34 integrally with the first sleeve member 30 such as by molding. It is also possible for the piercing members **34*a* and 34*b*** to be separate pieces that are connected together. It is also contemplated that one piercing member could be made of a polymeric material and the other piercing member made of metal.

The second sleeve member 32 has first and second end portions 80 and 82 respectively. The first end portion, 80 has a first diameter and the second portion 82, or proximal end, has a second diameter which is greater than the first diameter. In a preferred form, the first and second portions 80 and 82 are generally cylindrical in shape and are concentrically disposed to define a channel 83 in which the first sleeve 30 is received.

Figure 6:
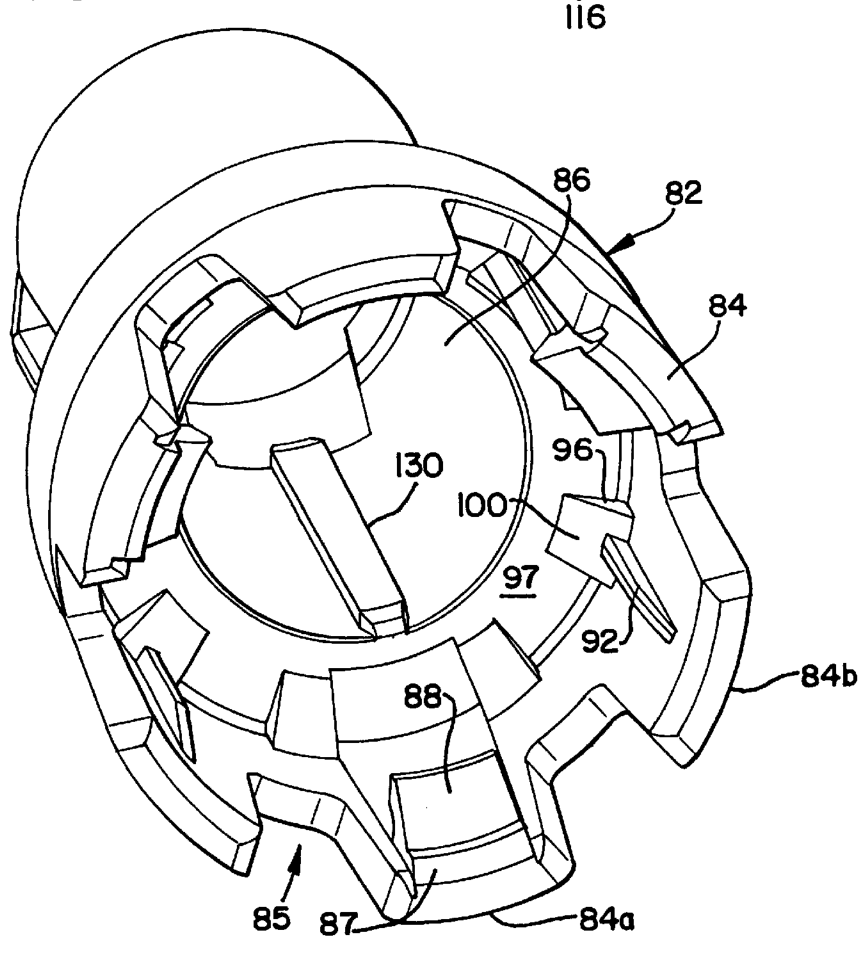
FIG. 6 is and end view of a vial connection end of the connector of the present invention.

Referring to FIG. 6, the second portion 82 of the second sleeve 32 preferably has means for attaching, and preferably means for fixedly attaching, the device to the vial 14 or a second attaching member. The means shown is six circumferentially disposed and axially extending segmented fingers 84 for connecting to the vial 14. The segmented fingers 84 are generally trapezoidal in shape and are separated by gaps 85 to define a vial receiving chamber 86 for receiving a top of the vial 14. Though the present device utilizes six segmented fingers 84, it can be appreciated by one of reasonable skill in the art that more or fewer fingers could be utilized without departing from the scope of the present invention.

What is meant by "fixedly attaching" is that in order to remove the vial from the connector one would have to exert a force considerably in excess of that normally used to operate the device. Such a force likely would break, detach or noticeably deform one or more of the segmented fingers 84 or other portions of the connector in the process..

As shown in FIG. 6, all of the fingers 84 include a flat lead-in section 87, which helps to properly align the vial 14 to be properly aligned with the second sleeve member 32 while being attached to the second sleeve member 32. Three of the fingers 84*a* also include, adjacent to the flat lead-in section 87, radially inwardly tapering resilient tabs 88, from a distal end to a proximal end, past which the medical professional must urge a neck 90 of the vial 14 in order to connect it to the second sleeve member 32. It can be appreciated that the tabs are capable of flexing and the fingers are capable of independently flexing to accommodate varying diameter vial closures. Preferably, the distal end of the fingers have a radiused end that is smooth to avoid cutting the medical personnel handling the connector. The tabs 88 shown have a space 89 between the distal end of the tab and the finger. However, the tabs 88 could also be formed as solid bumps without departing from the invention.

As best seen in FIG. 6, the remaining three fingers 84*b* have axially extending, standing ribs 92 extending from a generally wedge shaped gusset 96. The gusset 96 spaces the standing ribs 92 from the annular shelf 97. The front, axially-inward end of the gusset 98 is essentially flush with the annular shelf 97. The gusset has an upwardly sloping deck 100 from which the standing ribs 92 extend from a generally central portion thereof. In a preferred form, the standing ribs 92 extend axially-outwardly beyond a distal end of the tabs 88 to assist in aligning the vial with the vial receiving chamber 86 during insertion. The standing ribs 92 are capable of indenting one or more sidewall portions 102 of the metal crimp 26 of the vial 14 in order to inhibit the vial 14 the elastomeric closures 22 and 24 of the vial 14 and the flexible container 12 by the piercing member 34. Rotation of the vial can also cause the piercing member to pierce a sheath 106 which covers the piercing member 34.

While three fingers with resilient tabs 84*a* and three fingers with axial ribs 84*b* is preferred, providing more or fewer fingers with resilient tabs 88 or ribs 92 would not depart from the scope of the present invention. It is also preferable that the fingers with the tabs and the fingers with the standing ribs are disposed in alternating order. It may also be desirable to place a flexible restraining member, such as shrink wrap or the like, around the fingers 84 to assist in gripping the vial.

Located within the vial receiving chamber 86 and abutting the annular shelf 97 is a sealing member 103 having a disk 104 with a chamfer 105 on its peripheral edge. The disk 104 has a centrally disposed and axially extending sheath 106 that is dimensioned to fit over the piercing member 34. The sheath 106 has an enlarged distal end 107 that is dimensioned to fit over the hub 71. The enlarged end 107 has an increased cross-sectional thickness that increases the grip the sheath has on the hub 71. The sealing member 106 is made of an elastomeric material that is sufficiently deformable so that it does not exert pressure on the vial end to cause the piercing member 34 to move away from the vial stopper 24 when the connector is in the activated position. The sheath 106 has a low modulus so that it readily folds upon itself when the device is in the activated position. The sealing member 103 hermetically seals the piercing member 34 from contamination during storage and handling.

The sealing member 103 also forms a fluid-tight seal with a top of the vial 14. In a more preferred embodiment, the disk 104 further includes a centrally disposed, annular ridge 109 that extends axially in a direction opposite the sheath 106. The annular ridge 109 is dimensioned to tightly and sealingly fit over an aperture of the vial 14 to prevent leakage from the vial 14. The annular ridge 109 has an outwardly flaring sidewall 109*a* that forms a wiper seal with the closure of the vial. Further, centrally disposed within the annular ridge, where the sheath 106 joins the disk 104, the disk 104 has a portion 108 that has a reduced cross-sectional thickness for ease of piercing of the disk 104 by the piercing member 34.

Unlike the second jaw identified by reference numeral 74 in U.S. Pat. No. 4,675,020, discussed above, which is designed to contact a deformable end surface identified by reference numeral 94 of a drug vial to accommodate dimensional differences in the height of the crimp ring of a drug vial, the standing ribs 92 of the present invention do not contact a deformable end surface of the metal ring 26. Thus, the standing ribs do not account for dimensional differences in the distance between a shoulder of the vial and a deformable end surface. In fact, when the vial 14 is docked to the connector 10, the standing rib 92 cannot contact the deformable end surface of the vial as the deformable end surface is fully covered by the sealing member 103. Instead, the present device accounts for dimensional differences in the heights of the top of vials using the sealing member 103. The disk 104 and the sheath 106 of the flexible sealing member 103 deform to account for dimensional differences in the height of the top of a vial. Because of the expanded area, as well as the readily deformable nature of the disk 104 the sealing member 103 can account for a wider range of dimensional tolerances in the top of the vial and therefore is an improvement over the sharp projections of the second jaw of the '020 patent.

Figure 9:
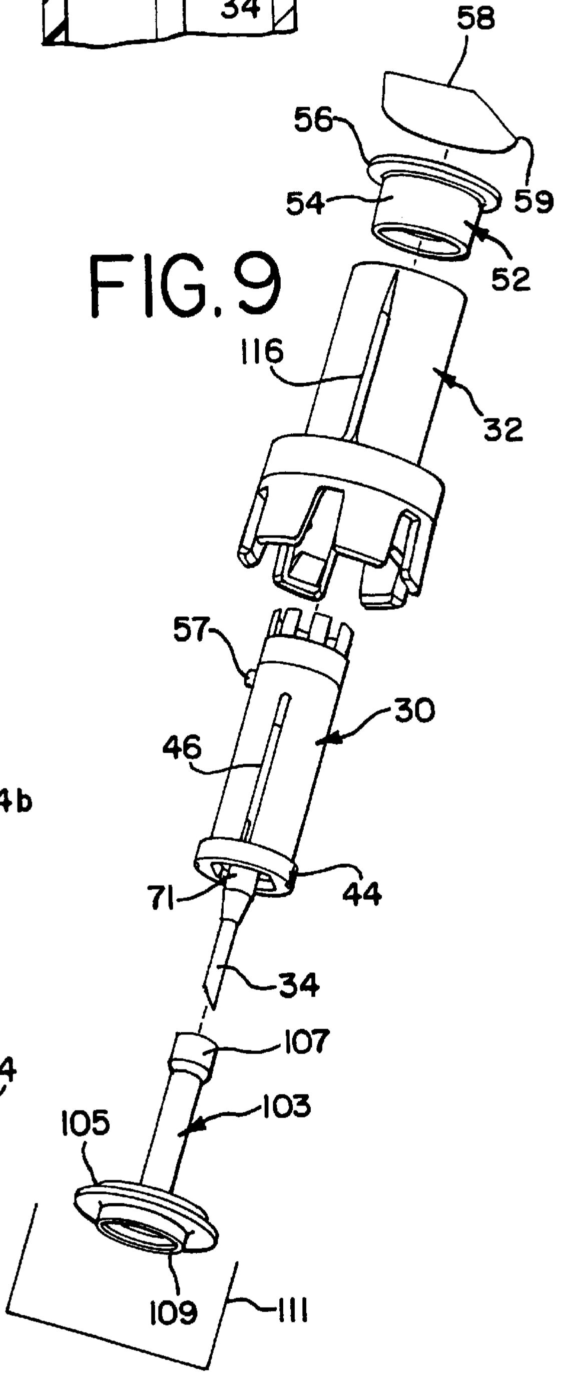
FIG. 9 is an assembly view in perspective of the connector of the present invention.

FIGS. 4 and 9 shows a means 111 for hermetically sealing the second end of the second sleeve 32. The means for sealing 111 operates independently of the means for sealing the first end of the first sleeve. That is to say that the means for sealing 111 can be removed while the first end 40 of the first sleeve 32 is sealed by the closure 58. The means 111 preferably is releasably attached to the second sleeve member 32 and is capable of providing a tamper evident indication that the sealing means has been removed. The sealing means 111 can be a cap that fits over the second end of the second sleeve 32, a barrier material such as a foil or polymeric material, a break away closure that is frangibly connected to the second sleeve member 32, a tear seal or the like.

FIGS. 2–4, and 9 also show that the second sleeve 32 has a sidewall 110 with an outer 112 and an inner surface 114. A set of opposed gripping ribs 116, circumferentially spaced 180 degrees from one another, extend along the outer wall, from a flange 118 defined at the junction of the first and second portions 80 and 82, to a top part of the first portion 80. The gripping rib 116 tapers 120 inwardly toward the sidewall 110 at it uppermost end 122. As will be explained below, the gripping ribs 116 provide a hand-hold to assist in rotating the first and second sleeve members 30 and 32 with respect to one another.

The device further includes means for visually indicating that the device is in the unlocked position. In a preferred form, the gripping ribs provide a visual indication that when aligned with the locking ribs 50 of the first sleeve 30, that the first and second sleeves 30 and 32 are positioned for axial movement.

Two axial activation ribs 130 are located on the inner surface 114 of the first portion 80 of the second sleeve 32. The activation ribs 130 extend from proximate the annular shelf 97 and terminate short of the uppermost end 122. The activation ribs 130 are circumferentially spaced 180 degrees from one another and each are positioned between the gripping ribs 116 on opposite sides of the second sleeve 32. The activation ribs 130 are dimensioned to fit within the activation grooves 46 to allow for relative axial movement of the first and second sleeve members 30 and 32.

As can be seen in FIGS. 2–5 and 9, a second flange 140 is provided on the inner surface 114 at the uppermost end 122 of the second sleeve 32. The second flange 140 extends axially downward and terminates short of a top of the activation ribs 130 to define a gap 142 therebetween. As shown in FIG. 2, when the connector 10 is in the inactivated position, the first flange 44 on the first sleeve 30 is positioned within the gap 142 and can rotate therein.

Figure 5:
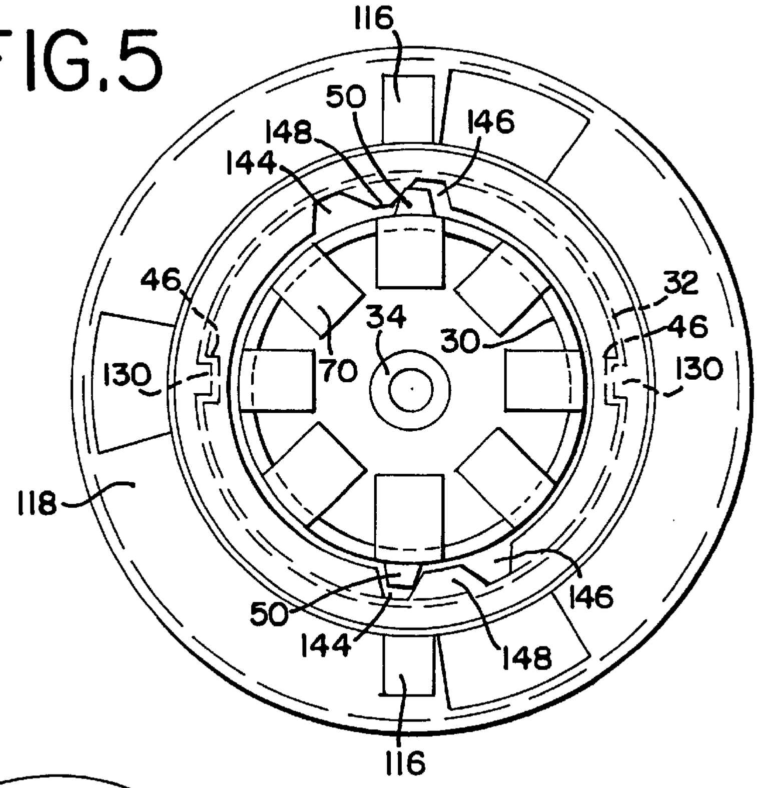
FIG. 5 is an end view of the connector of FIG. 4 taken along lines I—I.

The connector 10 further includes means for blocking axial movement of the first and second sleeve members. To this end and in a preferred form, the second flange 140 further includes first and second opposed sets of locking grooves 144 and 146 that are separated by a deformable protuberance 148. (FIG. 5). When the connector 10 is in the inactivated position, the locking ribs 50 of the first sleeve are located within either the first or second locking grooves 144 and 146. When the locking ribs 50 engage the first set of locking grooves 144, the activation ribs 130 will be out of alignment with the activation grooves 46 and will be blocked from axial movement by abutment of the first flange 44 and the activation ribs 130. Since no axial movement is possible in this position, the device 10 is in a locked position. FIG. 5 shows the activation ribs 130 in alignment with the activation grooves 46, thus the connector is in the unlocked position and ready for axial movement to the activated position. It can be appreciated that other means can be provided for blocking axial movement of the connector such as a cotter key that grips the first sleeve member 30 and abuts a top of the second sleeve member 32 to prevent axial movement until the cotter key is removed by medical personnel. It is also possible to apply tape or a shrink wrap material across the junction of the first and second sleeve members that must be removed before the sleeve members may be moved axially with respect to one another. Numerous other structures can be contemplated without departing from the present invention.

To move from the locked position to an unlocked position, the first member 30 is rotated with respect to the second member 32, thereby urging the locking ribs 50 past the protuberance 148, to bring the activation ribs 130 into alignment with the activation grooves 46. In urging the locking ribs 50 past the protuberance 148, the second sleeve 32 may temporarily take on an oval shape, as the locking ribs 50 contact the protuberances 148, to allow for the rotation of the first and second sleeve members 30 and 32. When in the unlocked position, the locking ribs 50 will be in alignment with the gripping ribs 116 to provide a visual indication that the connector 10 is in the unlocked position. In this position, the first and second sleeve members 30 and 32 can be moved axially into the activated position shown in FIG. 3.

Moving from the inactivated position (FIG. 2) to the activated position (FIG. 3), the first and second sleeves 30 and 32 are moved axially until the bushing 52 of the first sleeve 30 contacts the uppermost end 122 of the second sleeve to stop the axial movement. In this position, the enlarged portion 51 of the locking ribs 50 will lock into the locking groove 144 and form an interference fit therein. It can also be appreciated that unlike the device of the ’209 patent depicted in FIG. 1 that requires a third step to move it to a locked position, the present connector automatically locks upon being moved into the activated position.

Thus, once placed in the activated position, the connector cannot be moved back to an inactivated position. Further, while in the activated position, the first and second sleeve members will be blocked from relative rotational movement. Thus, it can be said that means are provided for automatically locking the connector in the activated position. The means for locking can be said to be responsive to movement of the connector into the activated position. The means for locking in the activated position also includes means for blocking the first and second sleeve members from relative rotational movement.

It can be appreciated that other structures could satisfy the means for locking the connector in the activated position such as providing an interference fit between the first and second sleeve members by tapering one of the sleeve members or by providing flanges on the first and second sleeve members that lock with one another when in the activated position.

Also, in the activated position the piercing member 34 pierces the closures 22 and 24 of the first and second containers 12 and 14 placing the containers in fluid communication to allow for reconstitution of the lyophilized drug in the vial 14.

The device 10 further includes a means for determining that the connector is in the activated position. In a preferred form, the means for determining is a color coding system wherein the first sleeve member 30 is one color, such as blue, and the second sleeve member 32 is another color, such as white. The bushing 52 is a different color than the first sleeve member 30. When the first sleeve member 30 and the second sleeve member 32 are fully in the activated position, none of the color of the first sleeve member 30, in this case blue, will be visible. If any of the color, in this case blue, shows, the medical personnel will immediately know that the device 10 is not fully activated.

To operate the present connector in a method for reconstituting a drug, the connector is removed from a packaging in which it is shipped, the foil barrier 58 is peeled from the bushing 52, and the port 20 of the flexible bag 12 is inserted into the central channel 35 of the first sleeve member 30. When inserting the port 20 into the first sleeve 30, the cannula 34 will puncture the septum 22 of the flexible bag 12. When the septum 22. is pierced and the diluent of the flexible bag 12 fills the cannula 34. However, at this point the flexible bag 12 and the vial 14 are not in fluid communication due to the disk 104 that blocks fluid flow through the cannula 34.

The medical professional will also remove the sealing means 111 from the second sleeve member 111 and fixedly dock the vial 14 into the receiving chamber 86. The connector may be docked to the container 12 and the vial 14 in either order.

Having both the vial 14 and the flexible container 12 docked and the septum 22 punctured, the medical professional will then rotate the first sleeve 30 in relation to the second sleeve 32, as described above, to place the device 10 in the unlocked position. Once the device 10 is in the unlocked position, the medical professional will move the first sleeve 30 axially in relation to the second sleeve 32 until the bushing 52 abuts the uppermost end 122 of the second sleeve member 32 causing an end of the cannula to puncture the rubber stopper 24 of the vial 4.

Once the rubber stopper 3 is punctured, the first and second containers 12 and 14 will be in fluid communication. The medical professional will then squeeze the flexible bag 12 to force fluid into the vial 14 to reconstitute the drug, shaking the vial 14 as necessary to facilitate reconstitution, and inverting the vial 14 in relation to the bag 12 to allow the reconstituted drug to flow back into the container.

It can be appreciated that certain steps of this method of reconstituting a drug may be unnecessary if the device is received preattached to the vial, preattached to the fluid container or preattached to both the vial and the flexible container.

Figure 7:
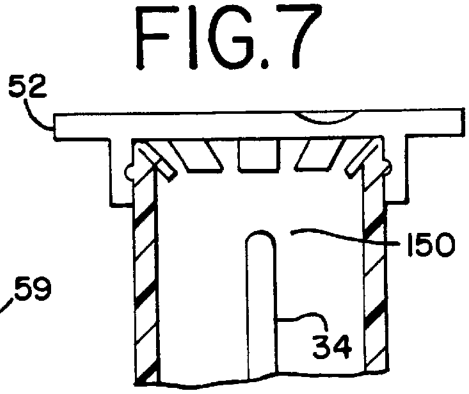
FIG. 7 is a cross-sectional view of a parenteral container connecting end of the connector having a blunt piercing member.

In another embodiment of the present container, the beveled end 73 of the cannula 34 could be replaced by a blunt end 150 as shown in FIG. 7.

Figure 8:
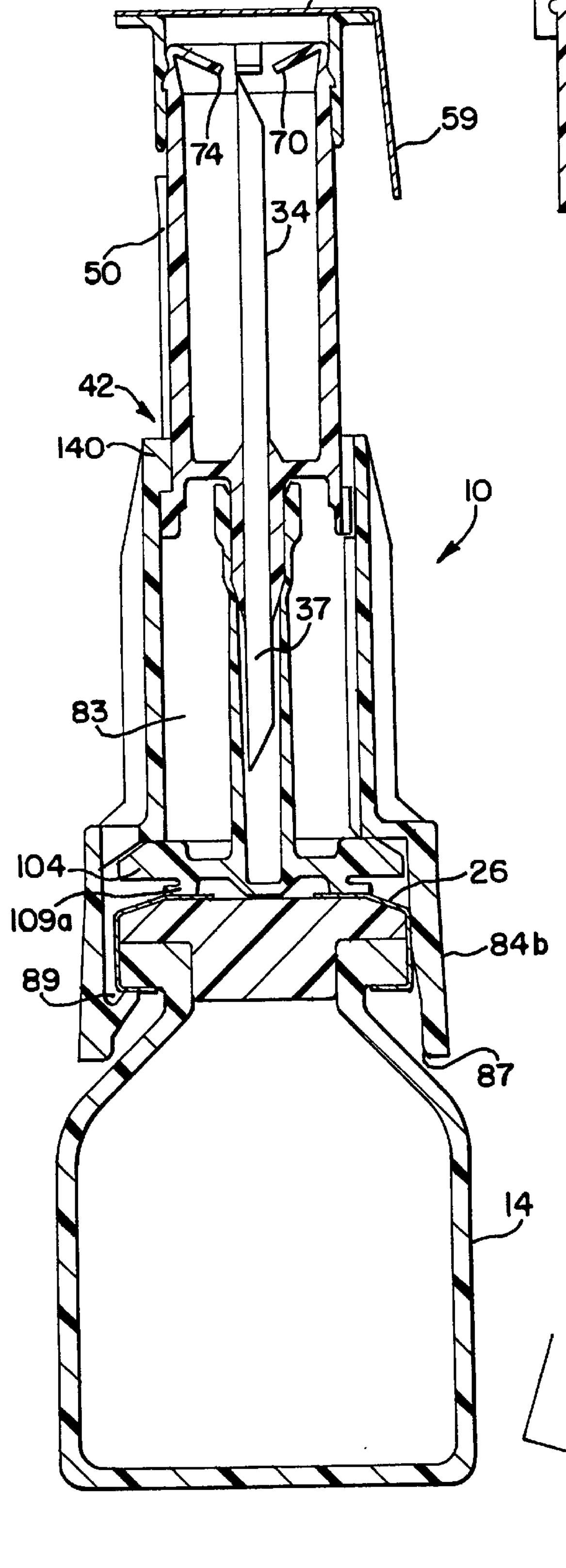
FIG. 8 is a cross-sectional view of the connector preconnected to a vial.

As shown in FIG. 8, it is possible to preattach the vial 14 to the connector 10 for shipment. Preattaching the vial 14 to the connector 10 may be accomplished using aseptic connecting techniques. The preferred method of preattaching the device 10 to the vial 14 include the steps of: 1) positioning the vial 14 and the second end 82 of the second sleeve 32 into opposed relationship, 2) simultaneously bringing the segmented fingers 84 into operative engagement with the vial 14 while sterilizing the connection by exposing the connecting portions of the device 10 and the vial 4 with, preferably, gamma sterilization or other sterilization energies or techniques, 3) locking the vial 14 to the connector. These steps can be carried out manually by medical personnel or automatically by a machine. The preattached vial 14 and connector 10 assembly may be wrapped in an outer pouch for shipping and storage.

While the specific embodiments have been illustrated and described, numerous modifications come to mind without significantly departing from the spirit of the invention, and the scope of protection is only limited by the scope of the accompanying claims.

I claim:

1. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable with respect thereto from an inactivated position to an activated position, the second sleeve member having at the second end an attaching member adapted to attach the second sleeve member to the second container, the attaching member having a plurality of circumferentially spaced and axially extending fingers collectively adapted to attach to the second container wherein one of the fingers has a standing rib adapted to contact a side portion of a closure of the second container; and a first piercing member and a second piercing member each projecting from one of the first and second sleeve members and providing a fluid flow path between the first container and the second container.

2. The device of claim 1 further comprising means for independently hermetically sealing the first and second piercing members.

3. The device of claim 2 wherein the means for sealing the first piercing member comprises:

a seal material releasably attached to the first end of the first sleeve member: and means for hermetically sealing the second piercing member.

4. The device of claim 2 wherein the means for sealing the second piercing member is a septum.

5. The device of claim 4 wherein the septum has a disk and a sheath extending axially away from the disk.

6. The device of claim 5 wherein the disk further comprises a centrally disposed annular ring axially extending in a direction away from the sheath, the annular ring being dimensioned to fit over a closure of the second container.

7. The device of claim 6 wherein the disk further comprises a centrally located piercing section having a smaller cross-sectional thickness than a portion of the septum outside the piercing section.

8. The device of claim 1 further comprising a means for locking the connector in the activated position.

9. The device of claim 8 wherein the means for locking comprises:

a first flange on the first end of the second sleeve;

a locking groove positioned on the flange of the first end of the second sleeve; and a locking rib on the exterior surface of the wall of the first sleeve, the locking rib extending axially along a portion of the wall for sliding in the locking groove, the locking rib having an enlarged portion proximate the first end of the first sleeve which forms an interference fit in the locking groove for locking the connector in the activated position.

10. The device of claim 1 wherein the first sleeve member is slidingly mounted within the second sleeve member for relative axial and rotational movement therein.

11. The device of claim 10 wherein the connector is movable between locked and unlocked positions, wherein in the locked position the first and second sleeve members are blocked from relative axial movement, and wherein in the unlocked position, the first and second connectors are capable of relative axial movement.

12. The device of claim 11 wherein the connector further comprises:

a pair of opposed activating grooves extending axially along a portion of the outer wall of the first sleeve member, and terminating short of the first end of the first sleeve member;

a first flange on the first end of the second sleeve member;

a pair of opposed activating ribs positioned on the interior surface of the second sleeve member and extending axially from proximate the second end and terminating short of the first flange to define a gap therebetween, the activating ribs are dimensioned to fit within the activating grooves to allow for relative axial movement of the first sleeve member with respect to the second sleeve member; and wherein in the locked position the activating ribs are out of alignment with the activating grooves and the first and second sleeve members cannot be moved axially with respect to one another and in the unlocked position the activating ribs are in alignment with the activating grooves and the first and second connector members can be moved axially with respect to one another.

13. The device of claim 11 wherein the connector is moved between the locked and the unlocked position by rotating the first sleeve member with respect to the second sleeve member.

14. The device of claim 13 further comprising a second flange at the second end of the first sleeve member, the second flange is dimensioned to fit within the gap and rotate therein.

15. The device of claim 10 further comprising means associated with the connector for preventing the first sleeve member from becoming disassociated from the second sleeve member when moving from the inactivated position to the activated position.

16. The device of claim 15 wherein the means for preventing the first and second sleeve members from becoming disassociated comprises a bushing connected to the first end of the first sleeve member.

17. The device of claim 10 further comprising:

a bushing connected to the first end of the first sleeve member, the bushing having an interior and exterior surface and a set of axially spaced annular ridges on the interior surface of the bushing.

18. A connector device for establishing fluid communication between a first container and a second container comprising:

a first sleeve member having a generally cylindrically shaped wall and a first and second end, the first sleeve member having at the first end a first attaching member adapted to attach to the first container;

an activating groove on an outer surface of the first sleeve member and extending axially from a second end of the first sleeve member and terminating short of the first end of the first sleeve member;

a second sleeve member having a first end and a second end and a generally cylindrically shaped sidewall, the sidewall having an interior surface and an exterior surface, the sidewall defining a channel for mounting the first sleeve member for axial movement therein from an inactivated position to an activated position, the second sleeve member having at the second end a second attaching member adapted to attach the second sleeve member to the second container;

an activating rib extending axially on the interior surface of the second sleeve member from a position proximate the second end of the second sleeve member and terminating short of the first end of the second sleeve member, the activating rib[s] being dimensioned to slide within the activating groove;

a first piercing member and a second piercing member each projecting from one of the first and second sleeve members and providing a fluid flow path between the first container and the second container;

means for independently hermetically sealing the first and second piercing members and means for locking the device in the activated position, the means for locking being responsive to moving the device into the activated position.

19. The device of claim 18 wherein the connector is movable from a locked position to an unlocked position where the first and second sleeve members are blocked from relative axial movement, and wherein in the locked position the first and second sleeve members are capable of relative axial movement.

20. The device of claim 19 wherein the device is moved from the locked to the unlocked position by rotating the first sleeve member with respect to the second sleeve member.

21. The device of claim 18 wherein the means for locking the device comprises means for preventing relative axial movement of the first and second sleeve members.

22. The device of claim 21 wherein the means for preventing relative axial movement is responsive to moving the device into the activated position.

23. The device of claim 22 wherein the means for preventing relative axial movement of the first and second sleeve members comprises an interference fit between the first and second sleeve members.

24. The device of claim 23 wherein the interference fit comprises:

a first flange on the first end of the second sleeve, the first flange extending axially downward and terminating short of a top of the activating ribs to define a gap therebetween;

a pair of opposed first and second locking grooves in the first flange, each of the first and second locking grooves being spaced from one another;

a set of locking ribs on the first sleeve member extending axially from the second end of the first sleeve member and terminating short of the first end of the first sleeve member, each of the locking ribs having an enlarged end proximate the first end of the first sleeve member, the locking ribs being dimensioned to slide within the first and second locking grooves;

a second flange on the second end of the first sleeve member that is positioned within the gap when in the activated position; and wherein the enlarged ends of the locking ribs provide an interference fit with the second locking grooves when in the activated position to prevent the device from being moved back to the inactivated position.

25. A connector device for establishing fluid communication between a first container and a second container, the device comprising:

a first sleeve member having a first end and a second end, the first sleeve member having at the first end a means for attaching to the first container;

a second sleeve member having a first end and a second end, the second sleeve member being associated with the first sleeve member and movable axially with respect thereto from an inactivated position to an activated position, the second sleeve member having at the second end a plurality of circumferentially spaced and axially extending fingers collectively adapted to attach to the second container wherein the fingers extend from an annular shelf;

at least one standing rib on one of the fingers adapted to contact a side portion of a closure of the second container, wherein the standing rib extends axially from a gusset on the annular shelf; and a first piercing member and a second piercing member each projecting from one of the first and second sleeve members and providing fluid flow between the first container and the second container.

26. The device of claim 25 further comprising means for locking the device in the activated position.

27. The device of claim 26 wherein the means for locking the device comprises means for preventing relative axial movement of the first and second sleeve members.

28. The device of claim 27 wherein the means for preventing relative axial movement is responsive to moving the device into the activated position.

29. The device of claim 27 wherein the means for preventing relative axial movement of the first and second sleeve members comprises an interference fit between the first and second sleeve members.

30. The device of claim 29 wherein the interference fit comprises:

a first flange on the first end of the second sleeve, the first flange extending axially downward and terminating short of a top of the activating ribs to define a gap therebetween;

a pair of opposed first and second locking grooves in the first flange, each of the first and second locking grooves being spaced from one another;

a set of locking ribs on the first sleeve member extending axially from the second end of the first sleeve member and terminating short of the first end of the first sleeve member, each of the locking ribs having an enlarged end proximate the first end of the first sleeve member, the locking ribs being dimensioned to slide within the first and second locking grooves;

a second flange on the second end of the first sleeve member that is positioned within the gap when in the activated position; and wherein the enlarged ends of the locking ribs provide an interference fit with the second locking grooves when in the activated position to prevent the device from being moved back to the inactivated position.

31. The device of claim 25 wherein the connector is movable from a locked position where the first and second sleeve members are blocked from relative axial movement to an unlocked position where the first and second sleeve members are capable of relative axial movement.

32. The device of claim 31 wherein the device is moved from the locked to the unlocked position by rotating the first sleeve member with respect to the second sleeve member.

33. A connector device for establishing fluid communication between a first container and a second container comprising:

a first sleeve member having a first end and a second end, the first sleeve member having at the first end a first attaching member adapted to attach to the first container;

a second sleeve member having a first end and second end, the second sleeve member being associated with the first sleeve member and movable with respect thereto from an inactivated position to an activated position, the second sleeve member having at the second end a second attaching member adapted to attach the second sleeve member to the second container;

a first piercing member and a second piercing member each projecting from one of the first and second sleeve members and providing a fluid flow path between the first container and the second container; and means for automatically locking the device in the activated position upon being moved into the activated position.

34. The device of claim 33 wherein the means for locking comprises:

a first flange on the first end of the second sleeve;

a locking groove positioned on the flange of the first end of the second sleeve; and a locking rib on the exterior surface of the wall of the first sleeve, the locking rib extending axially along a portion of the wall for sliding in the locking groove, the locking rib each having an enlarged portion proximate the first end of the first sleeve which forms an interference fit in the locking groove for locking the connector in the activated position.

35. The device of claim 33 wherein the means for locking further comprises means for blocking the first sleeve member and the second sleeve member from relative rotational movement.

36. A connector device for establishing fluid communication between a first container and a second container comprising:

a first sleeve member having a first end and a second end, the first sleeve member having at the first end a first attaching member adapted to attach to the first container;

a second sleeve member having a first end and second end, the second sleeve member being associated with the first sleeve member and movable with respect thereto from an inactivated position to an activated position, the second sleeve member having at the second end a second attaching member adapted to attach the second sleeve member to the second container;

a first piercing member and a second piercing member each projecting from one of the first and second sleeve members and providing a fluid flow path between the first container and the second container; and means for locking the device in the activated position, the means for locking being responsive to moving the device into the activated position.

37. A connector device for establishing fluid communication between a first container and a second container, the device comprising:

a first sleeve member having a first end and a second end, the first sleeve member having at the first end a means for attaching to the first container;

a second sleeve member having a first end and a second end, the second sleeve member being associated with the first sleeve member and movable axially with respect thereto from an inactivated position to an activated position, the second sleeve member having at the second end a receiving chamber and a plurality of circumferentially spaced and axially extending segmented fingers circumjacent the receiving chamber;

at least one standing rib on one of the fingers adapted to contact a side portion of a closure of the second container;

an annular shelf positioned within the receiving chamber, the standing rib extends from a gusset located on the annular shelf, and the standing rib extends axially outward to: a position proximate a distal end of the fingers;

a first piercing member and a second piercing member each projecting from one of the first and second sleeve members and providing fluid flow between the first container and the second container.

38. A connector device for establishing fluid communication between a first container and a second container, the device comprising:

a first sleeve member having a first end and a second end, the first sleeve member having at the first end a means for attaching to the first container;

a second sleeve member having a first end and a second end, the second sleeve member being associated with the first sleeve member and movable axially with respect thereto from an inactivated position to an activated position, the second sleeve member having at the second end a plurality of circumferentially spaced and axially extending segmented fingers collectively adapted to attach to the second container, at least one of the fingers having a tab having a distal end wherein a spaced is maintained between the distal end and the finger; and a first piercing member and a second piercing member each projecting from one of the first and second sleeve members and providing fluid flow between the first container and the second container.

39. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable with respect thereto from an inactivated position to an activated position, the second sleeve member having at the second end an attaching member adapted to attach the second sleeve member to the second container; and, a piercing member projecting from one of the first and second sleeve members and providing a fluid flow path between the first container and the second container, wherein the first sleeve member has a flange to prevent the first sleeve member from becoming disassociated from the second sleeve member.

40. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable with respect thereto from an inactivated position to an activated position, the second sleeve member adapted to attach to the second container;

a piercing member projecting from one of the first and second sleeve members and providing a fluid flow path between the first container and the second container; and, means for visually indicating that the connector is in the activated position comprising a color indication wherein the first sleeve member has a first color, and the second sleeve member has a second color perceptively different than the first color, wherein the first color is not visible when in the activated position.

41. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable with respect thereto from an inactivated position to an activated position, the second sleeve member having at the second end an attaching member adapted to attach the second sleeve member to the second container, the attaching member having six circumferentially spaced and axially extending fingers collectively adapted to attach to the second container wherein three extending fingers have standing ribs adapted to contact a side portion of a closure of the second container and three extending fingers have radially inwardly extending tabs, and;

a piercing member projecting from one of the first and second sleeve members and providing a fluid flow path between the first container and the second container.

42. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable in an axial direction with respect thereto from an inactivated position to an activated position, the second sleeve member having at the second end an attaching member adapted to attach the second sleeve member to the second container;

a piercing member projecting from one of the first and second sleeve members and providing a fluid flow path between the first container and the second container; and, a tape member positioned on the sleeves for preventing relative axial movement of the first and second sleeve members.

43. A connector device for establishing fluid communication between a first container and a second container comprising:

a first sleeve member having a first end and a second end, the first sleeve member adapted to attach to the first container;

a second sleeve member having a first end and second end, the second sleeve member being associated with the first sleeve member and movable in an axial direction with respect thereto from an inactivated position to an activated position, the second sleeve member having at the second end an attaching member adapted to attach the second sleeve member to the second container;

a piercing member projecting from one of the first and second sleeve members and providing a fluid flow path between the first container and the second container; and, a septum positioned proximate the second end of the second sleeve, the septum having a ridge extending therefrom and adapted to contact and form a seal against a closure of the second container.

* * * * *

UNITED STATES PATENT AND TRADEMARK OFFICE

CERTIFICATE OF CORRECTION

PATENT NO. : 6,610,040 B1 
DATED : August 26, 2003
INVENTOR(S) : Thomas A. Fowles et al.

It is certified that error appears in the above-identified patent and that said Letters Patent is hereby corrected as shown below:

Title page,
Item [56], References Cited, U.S. PATENT DOCUMENTS, "5,114,044" should be -- 5,114,004 --

Column 5,
Line 36, "a" (first occurrence) should be -- an --
Line 48, "and" should be -- an --

Column 7,
Line 65, "the." should be -- the --

Column 8,
Line 9, "a" (second occurrence) should be -- an --

Column 10,
Line 48, "shows" should be -- show --

Column 11,
Line 2, "it" should be -- its --

Column 12,
Line 58, "22." should be -- 22 --

Column 13,
Line 36, "4" should be -- 14 --

Column 14,
Line 9, ":" should be -- ; --

Column 15,
Line 48, "rib[s]" should be -- rib --
Line 55, "member" should be -- member, --

UNITED STATES PATENT AND TRADEMARK OFFICE

CERTIFICATE OF CORRECTION

PATENT NO. : 6,610,040 B1

DATED : August 26, 2003

INVENTOR(S) : Thomas A. Fowles et al.

It is certified that error appears in the above-identified patent and that said Letters Patent is hereby corrected as shown below:

<u>Column 19,</u>
Line 5, "spaced" should be -- space --

Signed and Sealed this

Fourteenth Day of December, 2004

JON W. DUDAS

*Director of the United States Patent and Trademark Office*